United States Patent [19]

Morita et al.

[11] 4,251,442

[45] Feb. 17, 1981

[54] METHOD FOR SYNTHESIS OF PENICILLIN

[75] Inventors: Yoshiharu Morita; Takaharu Itagaki, both of Yokohama; Tsuyoshi Ito, Machida; Shigenori Wada, Tokyo, all of Japan

[73] Assignee: Mitsubishi Chemical Industries Limited, Tokyo, Japan

[21] Appl. No.: 96,338

[22] Filed: Nov. 21, 1979

[30] Foreign Application Priority Data

Dec. 7, 1978 [JP] Japan ................... 53-151391

[51] Int. Cl.$^3$ ................................... C07D 499/12
[52] U.S. Cl. ......................................... 260/239.1
[58] Field of Search ................................ 260/239.1

[56] References Cited

U.S. PATENT DOCUMENTS

| 3,478,018 | 11/1969 | Robinson et al. | 260/239.1 |
| 3,479,338 | 11/1969 | Adams | 260/239.1 |
| 3,595,855 | 7/1971 | Robinson | 260/239.1 |
| 3,654,266 | 4/1972 | Robinson | 260/239.1 |
| 3,678,037 | 7/1972 | Robinson | 260/239.1 |
| 3,980,637 | 9/1976 | Grossman et al. | 260/239.1 |

*Primary Examiner*—Natalie Trousof
*Assistant Examiner*—Vera C. Clarke
*Attorney, Agent, or Firm*—Bierman & Bierman

[57] ABSTRACT

This invention relates to a method for synthesizing a penicillin by reacting a silylate of 6-aminopenicillanic acid and a carboxylic acid halide in the presence of an insoluble weakly basic resin having a three-dimensional structure.

5 Claims, No Drawings

METHOD FOR SYNTHESIS OF PENICILLIN

BACKGROUND OF THE INVENTION

1. Field of the Invention

This invention relates to a method for synthesizing a penicillin by reacting a silylate of 6-aminopenicillanic acid and a carboxylic acid halide, and more particularly it relates to such penicillin synthesizing method featuring use of a weakly basic resin as acid coupling agent.

2. Description of the Prior Art

It is known that various kinds of penicillin compositions can be synthesized from 6-aminopenicillanic acid and carboxylic acid halides. The reaction therefor is usually accomplished by first silylating 6-aminopenicillanic acid and then reacting the resultant silylate with a carboxylic acid halide. Since a hydrohalic acid is produced in this reaction, it needs to carry out the reaction in the presence of an acid coupling agent. Heretofore, amines such as dimethylamine, pyridine, quinoline, picoline, etc., have been commonly used as acid coupling agent in said reaction. However, use of such amines involves some serious problems: it is hard to separate such amines from the produced penicillin, and even if an elaborate separating operation is used, there still exists a possibility that a trace amount of amine should be mixed in the product penicillin. Presence of even a trace amount of amine in the product results in various adverse effects such as of causing headache, nausea, drowsiness, etc., because of toxicity of amines.

As a result of further researches into the penicillin synthesizing method with no need of using any amine, the present inventors found that the above-said problems can be solved by using an insoluble weakly basic resin having a three-dimensional structure as acid coupling agent, and succeeded in formulating the present invention.

SUMMARY OF THE INVENTION

It is an object of the present invention to provide a penicillin free of amines such as dimethylamine, pyridine, quinoline, picolin, etc.

According to this invention, a silylate of 6-aminopenicillanic acid and a carboxylic acid halide are reacted in a proper inert solvent in the presence of an insoluble weakly basic resin having a three-dimensional structure, and after removing the resin from the reaction mixture by filtration, centrifugation or other means, the object penicillin is separated from the filtrate and refined according to a known process, thereby obtaining a penicillin which is free of impurities and has no side effects.

DETAILED DESCRIPTION OF THE INVENTION

A silylate of 6-aminopenicillanic acid, which is one of the reaction materials in the process of this invention, can be easily obtained by silylating 6-aminopenicillanic acid with a silylating agent such as trimethylchlorosilane, triethylchlorosilane, triethylbromosilane, etc., in a suitable solvent such as benzene, toluene, methylene chloride, tetrahydrofuran, etc., and in the presence of a base such as triethylamine, diethylamine, ethylamine, etc., according to a known method.

The carboxylic acid halide to be reacted with said silylate of 6-aminopenicillanic acid may be suitably selected according to the type of the penicillin to be produced, but usually an acid halide of α-amino acid is used. In this case, it needs to protect the amino group of the acid halide with a pertinent protective agent such as for example a hydrohalic acid. Among the acid halides of α-amino acid, the phenylglycine derivatives represented by the following general formula (I) are most preferred.

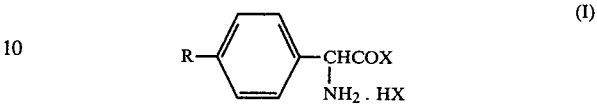

wherein R is hydrogen, a hydroxyl group or a protected hydroxyl group, and X is a halogen.

The insoluble weakly basic resin having a three-dimensional structure, which is also used in the reaction of this invention, may be selected from the copolymers of weakly basic polymerizable amines such as vinylpyridine, vinylquinoline, vinylpicoline, N,N-dimethylvinylaniline, etc., and polyfunctional monomers copolymerizable therewith. As the polyfunctional monomer, there may be used a trifunctional monomer such as trimethylolpropane trimethacrylate or other polyfunctional monomers of higher orders, but usually a difunctional monomer such as divinylbenzene, divinyltoluene, divinylnaphthalene, ethylene glycol dimethacrylate, divinyl adipate or the like is used. it is also possible to use a condensate of an amine such as dimethylaniline, N,N,N',N'-tetramethyl-m-phenylenediamine, etc., and an aldehyde such as formalin or glutaraldehyde. Among these weakly basic resins, those having a dissociation constant of from $10^{-8}$ to $10^{-11}$ are usually used in this invention. As regards the physical structure of the resin used in this invention, it is possible to use both of the so-called gel-structured type and the macro porous type having a large specific surface area. The particle size of the resin used in this invention is usually within the range of 20 to 400 meshes.

The reaction of a silylate of 6-aminopenicillanic acid with a carboxylic acid halide in the process of this invention can be accomplished in a generally known way except for use of said weakly basic resin instead of pyridine as acid coupling agent. Such reaction may be performed, for example, by adding a silylate of 6-aminopenicillanic acid, a substantially equimolecular amount of a carboxylic acid halide and at least equimolecular amount, preferably more than two equivalents of said dry, weakly basic resin in an inert solvent such as benzene, toluene, methylene chloride, ethylene chloride, tetrahydrofuran, ethyl ether, dimethylformamide, methylisobutyl ketone or the like. After the end of the reaction, resin is removed by filtration, centrifugation or other means and the reaction solution is added with water, alcohol or such to get rid of the silyl groups to produce a penicillin. Separation of the penicillin from the reaction solution and purification thereof can be accomplished according to a normal method that is suitably selected depending on the type of the penicillin to be produced. For instance, in the case of Ampicillin or Amoxycillin, the product can be precipitated in the form of crystals by adding caustic soda to the reaction solution to adjust pH of the reaction solution to the isoelectric point.

Since the penicillin obtained according to this invention is free of amines such as pyridine, use of the penicillin is not attended by any side effects.

The invention is now described in further detail by way of the examples as well as referential examples, but it is to be understood that the invention is not limited by these examples but may be embodied in other forms within the gist of the invention.

In the following referential examples, resin drying was effected at 80° C. under 1 mmHg for 8 hours.

The hydrochloric acid adsorptivity of the resin was determined in the following way: 3 g of the resin deprived of deposited moisture was added to 250 ml of a 1/5 N HCl solution, and after 18-hour shaking of the solution, the hydrochloric acid concentration of the supernatent liquid was measured to determine the amount of reduction from which the hydrochloric acid adsorptivity of the resin was calculated.

The dissociation constant of the resin was determined according to the method shown in F. Helfferich: "Ion Exchange" (McGraw-Hill, pub. in 1962) p. 84. Thus, the dissociation constant of resin in this invention is the apparent dissociation constant.

REFERENTIAL EXAMPLE 1

(Synthesis of gel type 4-vinylpyridine resin)

1,800 ml of desalted water, 72 g of common salt, 12 g of polyvinyl alcohol and 12 g of carboxymethyl cellulose were added and dissolved in a 3-liter four-necked flask adapted with a cooling pipe, a stirring rod and a nitrogen supply pipe, and after replacing the atmosphere in the flask with nitrogen, the mixture was further added with 4.26 g of industrial divinylbenzene (purity: 56.5%), 115.56 g of 4-vinylpyridine and 1.2 g of azobisisobutyronitrile. In the nitrogen atmosphere and under stirring, the mixture was heated at 80° C. for 4 hours and then at 90° C. for additional 4 hours to effectuate polymerization. After completion of the polymerization, the obtained resin was washed well with water. Then the resin was packed in a column and washed with 50 liters of methanol and then with 10 liters of water. This was followed by further washing with 50 liters of 1 N hydrochloric acid, 10 liters of desalted water, 50 liters of 1 N caustic soda and 30 liters of desalted water successively in that order. The hydrochloric acid adsorptivity of the obtained resin was 2.99 meq/ml (wet resin) and 9.11 meq/g (dry resin), and the moisture content was 50%. The dissociation constant of this resin at 20° C. was $9.7 \times 10^{-10}$ and the particle size was 100–200 meshes.

REFERENTIAL EXAMPLE 2

(Synthesis of highly porous type 4-vinylpyridine resin)

1,500 ml of desalted water, 90 g of common salt and 2 g of polyvinyl alcohol were added and dissolved in a 3-liter four-necked flask provided with a cooling pipe, a stirring rod and a nitrogen supply pipe, and after replacing the atmosphere in the flask with nitrogen, there were further added 53.1 g of industrial divinylbenzene (purity: 56.5%), 66.9 g of 4-vinylpyridine, 12 g of benzoyl peroxide and 48 g of isooctane. The mixture was heated at 80° C. for 4 hours and then at 90° C. for additional 4 hours in the nitrogen atmosphere under stirring to effectuate polymerization. Upon completion of the polymerization, the obtained resin was washed in the same way as Referential Example 1. The hydrochloric acid adsorptivity of the thus obtained resin was 1.19 meq/ml (wet resin) and 6.22 meq/g (dry resin) and the moisture content was 67.9%. The dissociation constant of this resin at 20° C. was $8.4 \times 10^{-10}$ and the particle size was 50–100 meshes.

EXAMPLE 1

43.2 g (0.20 moles) of 6-aminopenicillanic acid and 40.5 g (0.40 moles) of triethylamine were added into 500 ml of methylene chloride, and the mixture was stirred at room temperature for 45 minutes. Then, after adjusting the temperature to 15° C., the mixture was further added with 43.4 g (0.40 moles) of trimethylchlorosilane over the period of 7 minutes and then stirred at 40° C. for 60 minutes to complete the silylation.

The reaction mixture was cooled to −25° C., added with 87.8 g (0.8 equivalents) of the dry resin produced in Referential Example 1 and then further added dropwise with 43.3 g (0.20 moles) of D(−)-α-phenylglycylchloride hydrochloride (purity: 95%) over the period of 60 minutes. After the end of this dropwise addition, the temperature was raised to −5° C. and the mixture was stirred at this temperature for 90 minutes. The resin was filtered out and washed with 200 ml of cold methylene chloride, and the wash liquid was joined with the filtrate. Methylene chloride was evaporated from the filtrate at 0° C. under reduced pressure until the liquid quantity became 400 ml, and then the filtrate was poured into 400 ml of cold water and stirred for 10 minutes. The mixed solution was allowed to stand still to cause separation into two layers, and the methylene chloride layer was reextracted with 50 ml of cold water. This was joined with the aqueous layer and added with 280 ml of methylisobutyl ketone. After adjusting pH to 4.5 with a 20% caustic soda solution, the mixture was stirred at 10° C. for one hour. The precipitated crystals were filtered out, washed twice with 75 ml of water and thrice with 125 ml of acetone and then dried at 35° C. under reduced pressure. The thus obtained Ampicillin trihydrate had purity of approximately 90% (purity according to microbial activity) and the yield was 57%.

EXAMPLE 2

The 6-aminopenicillanic acid silylation reaction mixture obtained in the same way as Example 1 was cooled to −25° C., then added with 128.6 g (0.80 equivalents) of the resin produced in Referential Example 2 and further added dropwise with 55.5 g (0.20 moles) of D(−)-α-(p-hydroxyphenyl) glycinechloride hydrochloride (purity: 80%) over the period of 60 minutes. Upon completion of this dropwise addition, the temperature was raised to −5° C. and the mixture was stirred at this temperature for 90 minutes to complete the reaction. This was followed by the same treatment as Example 1 except that pH was adjusted to 5.3 at the time of precipitation. There was consequently obtained Amoxycillin trihydrate with purity of 88%.

REFERENTIAL EXAMPLE 3

(Synthesis of gel type 2-vinylpyridine resin)

1,800 ml of desalted water, 150 g of common salt, 2 g of polyvinyl alcohol, 8.9 g of divinylbenzene (purity: 56.5%), 243.1 g of 2-vinylpyridine and 2.5 g of azobisisobutyronitrile were added to a 3-liter four-necked flask equipped with a cooling pipe, a stirring rod and a nitrogen supply pipe, and the mixture was heated at 65° C. for 4 hours and then at 80° C. for 5 hours in the nitrogen atmosphere under stirring to perform polymerization. After completion of the polymerization, the obtained resin was washed in the same way as Referential Example 1. The resultantly obtained resin had hydrochloric acid adsorptivity of 3.32 meq/ml (wet) and 8.78 meq/g (dry) and moisture content of 45.3%. The dissociation constant of this resin at 20° C. was $5.0 \times 10^{-11}$ and the particle size was 100-200 meshes.

REFERENTIAL EXAMPLE 4

(Synthesis of highly porous 2-vinylpyridine resin)

1,500 ml of desalted water, 126 g of common salt and 1.6 g of polyvinyl alcohol were added and dissolved in a 3-liter four-necked flask furnished with a cooling pipe, a stirring rod and a nitrogen inlet pipe, and after replacing the interior of the flask with nitrogen, there were further added 111 g of divinylbenzene (purity: 56.5%), 99 g of 2-vinylpyridine, 210 g of toluene, 42 g of polystyrene and 2.1 g of azobisisobutyronitrile. The mixture was then heated at 65° C. for 4 hours and then at 80° C. for additional 5 hours in the nitrogen atmosphere under stirring to accomplish polymerization. After completion of the polymerization, the resin was filtered out and stirred in 1 liter of toluene for 3 hours, and after extracting the polystyrene portion, the resin was further filtered out. The similar extraction operation was repeated again, and the resultantly obtained resin was washed in the completely same way as Referential Example 1. The thus obtained resin and hydrochloric acid adsorptivity of 1.37 meq/ml (wet resin) and 4.30 meq/g (dry resin) and moisture content of 54.0%. The dissociation constant of this resin was $3.9 \times 10^{-11}$ and the particle size was 20-100 meshes. The specific surface area and pore volume of this resin were 37 m²/g-resin and 0.548 ml/g-resin, respectively.

REFERENTIAL EXAMPLE 5

100 g of macro porous chloromethylated crosslinked polystyrene with chlorine content of 11.2%, specific surface area of 102 m²/g and pore volume of 1.24 ml/g was immersed in 400 g of dioxane, and after 30-minute standing at room temperature, the solution was further added with 28.6 g of a 30% caustic soda solution and 66.2 g of imidazole and stirred at 90° C. for 8 hours to effectuate the reaction. Upon completion of the reaction, the obtained resin was washed in the completely same way as Referential Example 1. The resultant resin had hydrochloric acid adsorptivity of 0.622 meq/ml (wet resin) and 2.28 meq/g (dry resin) and moisture content of 59.4%. The dissociation constant of this resin was $1.95 \times 10^{-9}$ and the particle size was 20-100 meshes. Also, the specific surface area and pore volume of this resin were 51.5 m²/g and 1.18 ml/g, respectively.

EXAMPLE 3

10.8 g of 6-aminopenicillanic acid, 10.1 g of triethylamine and 6.26 g of the dry resin produced in Referential Example 3 were added to 100 ml of dichloromethane, and the mixture was stirred at room temperature for 30 minutes. After adjusting the temperature to 15° C., the mixture was further added with 10.85 g of trimethylchlorosilane at 15° C. over the period of 5 minutes and stirred at 40° C. for 2 hours to complete the silylation.

The reaction mixture was cooled to −15° C. and added dropwise with 10.33 g of D(−)-α-phenylglycylchloride hydrochloride for the period of 10 minutes. Thereafter, the mixture was stirred at −15° C. for 1.5 hours and then, after heating to 15° C., further stirred at this temperature for 1.5 hours. Upon completion of the reaction, resin and insolubles were filtered out, and the filtered material was washed with 50 ml of cold dichloromethane. The wash liquid was joined with the filtrate.

This solution was added with 100 ml of cold water of 0° C. and stirred for 15 minutes. It was then allowed to stand still to cause separation into two layers. After filtering out the insolubles of the water layer, pH of the water layer was adjusted to 4.5 by adding 27% ammonia water and the mixed solution was stirred at 10° C. for one hour. The precipitated crystals were filtered out, washed with 20 ml of cold water (0° C.) and then with 50 ml of acetone and thereafter dried at 30° C. under reduced pressure for 10 hours. There was resultantly obtained an Ampicillin trihydrate in a yield of 56% and with purity (according to microbial activity) of 91.7%.

EXAMPLE 4

Ampicillin trihydrate was synthesized by following the completely same procedure as Example 3 except for use of 12.8 g of the dry resin produced in Referential Example 4 instead of the resin produced in Referential Example 3. The yield of said Ampicillin trihydrate was 60% and the purity according to microbial activity was 94.6%.

EXAMPLE 5

Ampicillin trihydrate was synthesized in the completely same way as Example 4 except for use of 24.1 g of the dry resin produced in Referential Example 5 instead of the resin produced in Referential Example 3. The yield of said Ampicillin trihydrate was 51% and the purity according to microbial activity was 93.4%.

Comparative Example 1

The process of Example 3 was repeated but by using 6.66 g of dimethylaniline instead of the resin produced in Referential Example 4 to synthesize Ampicillin trihydrate.

The yield of said Ampicillin trihydrate was 75%, but presence of 14,000 ppm of dimethylaniline was detected in said Ampicillin trihydrate.

We claim:

1. A penicillin synthesizing method comprising reacting a silylate of 6-aminopenicillanic acid and a carboxylic acid halide in the presence of an insoluble weakly basic resin having a three-dimensional structure and a dissociation constant of from $10^{-8}$ to $10^{-11}$.

2. A penicillin synthesizing method according to claim 1, wherein the carboxylic acid halide is a halide of α-amino acid having its amino group protected.

3. A penicillin synthesizing method according to claim 1, wherein the carboxylic acid halide is a phenylglycine derivative represented by the following general formula:

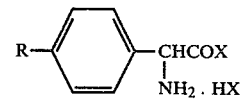

wherein R is hydrogen, a hydroxyl group or a protected hydroxyl group, and X is a halogen.

4. A penicillin synthesizing method according to claim 1, wherein the weakly basic resin is a polyvinylpyridine.

5. A penicillin synthesizing method according to claim 1, wherein the weakly basic resin is a reaction product of cross-linked polystyrene and imidazole.

* * * * *